(12) United States Patent
Esin et al.

(10) Patent No.: US 8,384,018 B2
(45) Date of Patent: Feb. 26, 2013

(54) INCREASE OF NEUTRON FLUX WITH GAMMA SHIELDING

(75) Inventors: Alexander Joseph Esin, Sugar Land, TX (US); Nikolay Baturin, Sugar Land, TX (US); Alex Kulik, Sugar Land, TX (US); Michael G. Brosseau, Baytown, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 142 days.

(21) Appl. No.: 12/852,032

(22) Filed: Aug. 6, 2010

(65) Prior Publication Data

US 2012/0032091 A1    Feb. 9, 2012

(51) Int. Cl.
    *G01V 5/10*    (2006.01)
(52) U.S. Cl. .................................................. 250/269.4
(58) Field of Classification Search ............... 250/269.4, 250/269.5, 370.05, 390.01, 518.1
    See application file for complete search history.

(56) References Cited

U.S. PATENT DOCUMENTS

| | | | |
|---|---|---|---|
| 2,778,950 A | 1/1957 | Frey et al. | |
| 3,955,087 A | 5/1976 | Ashe | |
| 5,481,105 A * | 1/1996 | Gold | 250/266 |
| 7,276,715 B2 * | 10/2007 | Climent et al. | 250/506.1 |
| 2002/0170348 A1 * | 11/2002 | Roscoe et al. | 73/152.02 |
| 2002/0175288 A1 | 11/2002 | Taleyarkhan | |
| 2006/0043308 A1 * | 3/2006 | Mcgregor et al. | 250/370.05 |
| 2007/0095157 A1 * | 5/2007 | Lingren et al. | 73/863 |
| 2007/0160176 A1 * | 7/2007 | Wada | 376/158 |
| 2007/0241275 A1 * | 10/2007 | Guo et al. | 250/269.1 |
| 2009/0242746 A1 * | 10/2009 | Pemper et al. | 250/269.6 |

FOREIGN PATENT DOCUMENTS

GB        2423577 A        8/2006

OTHER PUBLICATIONS

Combined Search and Examination Report filed in corresponding Great Britain Application No. GB1113366.7; Dated Apr. 5, 2012 (7 pages).

* cited by examiner

*Primary Examiner* — Mark R Gaworecki
(74) *Attorney, Agent, or Firm* — Osha Liang LLP (57) ABSTRACT

An analyzer having a detector and a neutron source assembly adjacent to the detector is disclosed, wherein the neutron source assembly has a neutron source and a shielding source holder.

20 Claims, 7 Drawing Sheets

INCREASE OF NEUTRON FLUX WITH GAMMA SHIELDING

FIELD OF INVENTION

Embodiments disclosed herein relate generally to high-energy radiation detection. In particular, embodiments disclosed herein relate to separation of neutron signal from gamma signal. Specifically, it is found that certain materials used to stop gamma rays also can increase the neutron flux to the detector.

BACKGROUND

Neutron flux is typically measured by the effect of interactions between neutrons and their surroundings. For example, neutrons may interact with a material to be detected, and thus create a measurable effect. Detectors may be used to detect such effects, which may include high-energy and ionizing radiations resulting from absorptive reactions, activation processes, and elastic scattering reactions, for example. "High-energy radiation," as used herein, refers to radiation of neutrons, X-rays, gamma rays, α particles, and β particles.

Figure 1:
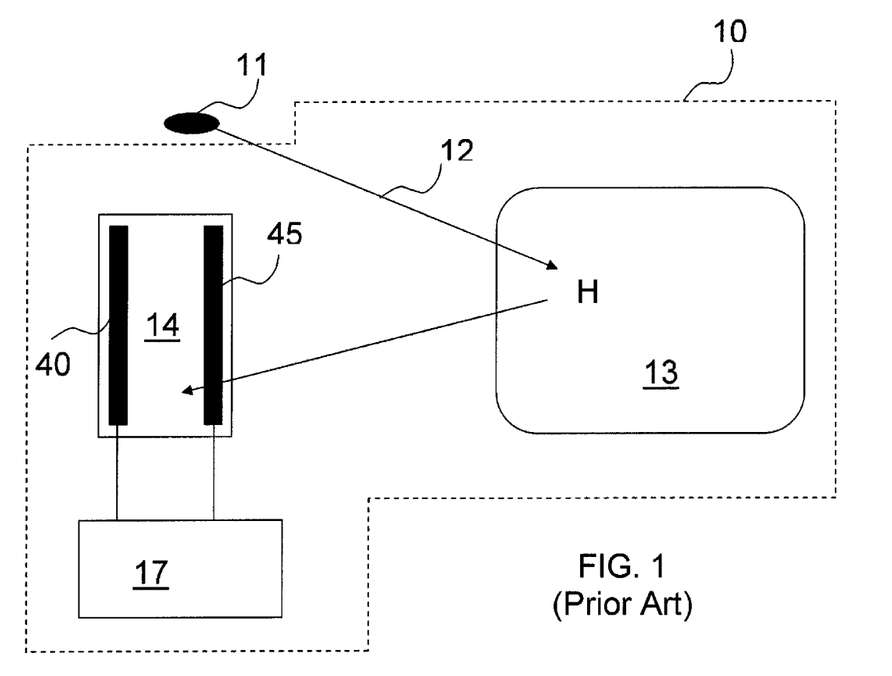
FIG. 1 shows a schematic of a conventional neutron detection system.

Detectors of high-energy radiation may include, for example, ion chambers, proportional counters, Geiger-Mueller counters, and scintillation counters. FIG. 1 shows an exemplary prior art detector that may be used to measure hydrogen content by detecting thermal neutrons reflected back from a target. As shown, a basic system 10 for neutron detection includes a target chamber 13, an ion chamber 14, and electronics (not independently illustrated). Fast neutrons 12 are produced by a neutron source 11. These fast neutrons 12 interact with hydrogen nuclei H in the target chamber 13 until their velocity is reduced to the average thermal velocity of the target through a process known as neutron moderation. Specifically, neutron moderation involves a collision and energy transfer from a fast neutron to a target nucleus, wherein the velocity of the fast neutron decreases to that of a slow neutron after the collision and energy transfer. The thermal (slow) neutrons are then scattered from the target chamber 13 to the ion chamber 14.

In the example of a commonly used neutron detector shown in FIG. 1, the ion camber 14 may be filled with a gas (such as He-3) that may interact with the thermalized neutrons to produce ions. When a He-3 atom absorbs (captures) a thermalized neutron, a nuclear reaction occurs and the resultant products are a positively ionized tritium (H-3) atom and a proton. The positively ionized H-3 atoms and protons travel through the gas, pulling electrons in their wake and thus creating an equal number of positive ions and electrons. When a potential is applied across the electrodes 40, 45 in the ion chamber 14, the positive ions are swept to the negatively charged electrode and the electrons are swept to the positively charged electrode, producing currents that are directly proportional to the number of ions transferred. The number of ions transferred depends on the rates of their formation and hence the neutron flux. Thus, the ion currents measured by the ion chamber may be used to derive the magnitudes of the neutron flux, which may be used to determine the amount of hydrogen in the target material.

However, the ion currents generated in these processes are extremely small (on the order of $10^{-12}$ amp), making it difficult to accurately determine neutron flux. In addition, temperature and humidity changes in various electronic components, cables, etc. may further compromise the accuracy of the measurements. The situation is even worse under field conditions, which often include wide variations in temperature and humidity.

While prior art high-energy radiation detectors are capable of providing satisfactory measurements, there remains a need for detectors that may provide more reliable and accurate measurements of high-energy radiations.

SUMMARY OF INVENTION

In one aspect, embodiments disclosed herein relate to an analyzer having a detector and a neutron source assembly adjacent to the detector, wherein the neutron source assembly has a neutron source and a shielding source holder.

In another aspect, embodiments disclosed herein relate to a method for measuring neutron signals that includes detecting background in a detector system, placing a target comprising a moderating material within the detector system, measuring a total signal for the detector system, and determining the neutron signal for the detector system.

Other aspects and advantages of the invention will be apparent from the following description and the appended claims.

DETAILED DESCRIPTION

Embodiments of the invention relate generally to detector systems for measuring high-energy radiation, and in particular for increasing and measuring neutron flux. Neutron flux, as used herein, refers to the amount of neutrons passing through an area over a period of time. Detector systems used for measuring neutron flux may rely on neutron moderation, i.e., a process of bringing fast neutrons into thermal equilibrium. In particular, as neutrons are generated from a neutron source, the neutrons are released having high kinetic energy, which are referred to herein as "fast neutrons." In accordance with energy conservation laws, the high kinetic energy of fast neutrons may be reduced (moderated) by colliding with and transferring energy to moderator material. Upon transferring energy to a moderator material, the speed at which fast neutrons travel reduces, thus giving the post-collision neutrons the name slow neutrons. Due to the relationship between neutron kinetic energy and neutron temperature, slow neutrons may also be referred to as thermal neutrons after fast neutron moderation.

Further, using moderator material having a low atomic number may allow for more efficient energy transfer. For example, the collision of a fast neutron with a hydrogen nucleus, which has substantially similar atomic mass as a neutron, may result in substantial reduction of energy in the fast neutron, thereby generating slow detectable neutrons at a faster rate. Accordingly, detector systems may use hydrogen-containing moderator materials (like water) for neutron moderation and detection. Additional examples of moderator material include graphite, polyethylene, polypropylene, polystyrene, and other plastics, alcohol, oil, and other organic material, coke, iron pellets, hydrocarbon material, and other materials having a low atomic number, high scattering cross section, and low absorption cross section. As used herein, hydrogen-containing materials refer to a type of moderator material. However, regardless of the target material, embodiments disclosed herein allow for increased measurements of neutron flux while also providing gamma shielding.

Such detection processes may likewise be used for moisture analysis. For example, embodiments of the present disclosure may utilize mathematical correlations between the amount of slow neutrons detected (i.e., neutron flux) from neutron moderation with a hydrogen-containing material such as water to provide information regarding the amount of hydrogen nuclei present, and thus provide means for analysis regarding the amount of moisture present.

Figure 2:
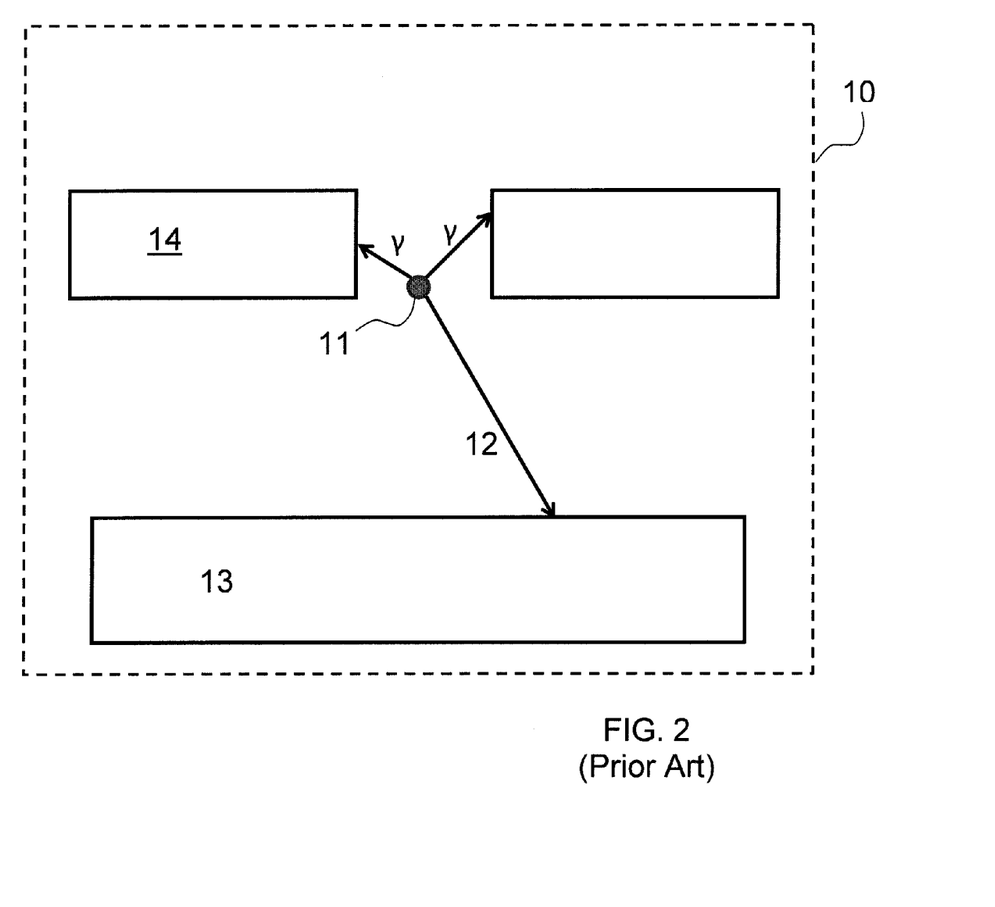
FIG. 2 shows a cross-sectional view of a conventional moisture analyzer.

FIG. 2 shows a conventional moisture analyzer 10 having a toroidal (donut) shape detector 14 with a neutron source 11 disposed within the detector 14. As shown, neutron source 11 generates fast neutrons 12 and gamma rays γ. For example, along with emitting fast neutrons, a commonly used neutron source, americium-beryllium (AmBe), may emit about 4.43 MeV γ. Other neutron sources may include americium-lithium (AmLi), radium-beryllium (RaBe), or plutonium-beryllium (PuBe), for example. Other industrial neutron sources include a neutron generator which is a direct action electrostatic accelerator (ion gun). In a neutron generator, deutrons accelerated to about 80 keV may hit a deuteron or tritium target, the collision of which may produce neutrons. These sources may be more powerful than the isotopic sources but more expensive and with a shorter life than Am/Be. Thus, a neutron generator may commonly be used where the desired high neutron flux cannot be achieved with isotopic sources. Additionally, a neutron generator may be capable of operating in a pulse mode.

A fraction of the fast neutrons 12 emitted from neutron source 11 will scatter into the target chamber 13, which may be filled with hydrogen-containing materials (like water). The fast neutrons 12 collide with the hydrogen nuclei in the target chamber 13. Hydrogen nuclei, with a similar mass as that of a neutron, are very efficient in slowing down the fast neutrons and eventually bringing them into thermal equilibrium with the environment (neutron moderation). As a result of the interactions with hydrogen nuclei, fast neutrons lose kinetic energy and become slower (thermal) neutrons. For example, upon interactions with hydrogen nuclei, thermal neutrons may have an average energy equal to the energy of thermal motion (25 meV) at room temperature. Thermal neutrons may then undergo diffusion similar to gas diffusion, and some of the thermal neutrons may return to the detector 14 to be measured as neutron flux.

Detector 14 is an ion chamber filled with a gas having nuclei that can capture thermal neutrons and undergo nuclear reactions after neutron capturing. Such nuclei include: boron (B-10, e.g., $BF_3$), lithium (Li-6), helium (He-3), uranium-233, uranium-235, and plutonium-239. Among these, He-3 gas has the advantage of having a large thermal neutron cross section (5330 barns) and, therefore, is commonly used in the ion chamber. Although B-10 (used in $BF_3$ reactions with neutrons) has a lower thermal neutron cross section (3840 barns) than He-3, $BF_3$ may also commonly be used in the ion chamber due to its availability. However, one of ordinary skill in the art would appreciate that embodiments of the invention are not so limited. In fact, embodiments of the invention may use any gas or other medium capable of ion transport that can produce ions by the high-energy radiation of interest.

Detector 14 is sensitive mostly to thermal neutrons and much less so to fast neutrons 12 and gamma rays γ. However, detected thermal neutron flux may be lower since only a few neutrons come back to the detector due to diffusion. The result of relatively high gamma detection is referred to as gamma background, which may contribute to total background noise, i.e., detector signals not related to the presence of hydrogen. Background noise is typically higher in $BF_3$-filled detectors than in a He-3-filled detectors.

Neutron flux may be measured in an ion chamber detector by applying an electric potential across a pair of electrodes in the ion chamber. For example, in an He-3-filled detector, two electrodes may be positioned parallel within the detector to measure current flowing in the He-3 gas as a potential is applied between the electrodes. He-3 gas typically serves as an insulator, and, therefore, no current (except for a small leakage current) is detectable between the two electrodes. However, when an He-3 atom absorbs (captures) a thermal neutron, a nuclear reaction occurs as follows:

$$_2^3He + _0^1n \rightarrow _1^3H + _1^1p \qquad (1)$$

This nuclear reaction produces a tritium (H-3) atom and a proton. He-3 and H-3 are isotopes of helium and hydrogen, respectively. This reaction also releases an energy of approximately 764 keV (i.e., Q-value=764 keV), and, therefore, the tritium and the proton are produced with high kinetic energy. The tritium and proton travel at high speeds through the gas, pulling electrons in their wake to create an equal number of positive ions and electrons. The positive ions and electrons serve as charge carriers in the gas, which is otherwise an insulator.

If a voltage is applied across a pair of electrodes within an ion chamber detector, an electric field is created in the space between the electrodes. The ions move in response to this electric field with the positive ions and electrons pulled in opposite directions toward opposite electrodes. The ions are eventually neutralized at the electrodes, resulting in an ion current that is directly proportional to the number of positive ions transferred to the electrodes. Such an ion current may be measured. Further, the number of positive ions transferred to the electrodes is in turn proportional to the thermal neutron flux. Therefore, the ion current measured from the electrodes may be used to derive the magnitude of the thermal neutron flux through ion chamber.

The positive ions and electrons present in the ion chamber may also collide and then recombine to form a neutral atom. This recombination competes with ion and electron transport to the electrodes, and, thus, reduces the measurable magnitudes of the ion currents. In the absence of an applied voltage across the ion chamber, there will be no ion transport and the positive ions and electrons will eventually recombine. When voltage is applied across the electrodes, the positive ions are pulled toward the negatively charged electrode and the electrons are pulled toward the positively charged electrode, reducing the probability of recombination. If the voltage applied across the electrodes is too small, the positive ions and electrons travel slowly to the electrodes, resulting in more recombination. When the voltage is high enough to pull the electron and ion clouds apart and make recombination insignificant, a "plateau" (also referred as "ion plateau" or "first plateau") begins to form. The plateau ends when the voltage is high enough to accelerate the electrons to the energy high enough to ionize gas atoms upon collision (secondary ionization). This process is known as "proportional regime," and may be used in proportional counters. However, ion chamber detectors generally do not exhibit proportional regime, and work on plateau with the current independent of voltage since primary ionization may be collected without recombination.

Advantageously, the inventors of the present disclosure have found that by using a shielding material, in particular a shielding source holder, between a neutron source and a detector, the detector may be shielded from gamma rays (thus decreasing gamma background) and neutron flux may be enhanced. For example, along with suppressing the gamma background, shielding source holders made of lead (Pb) and tungsten (W) may also increase the neutron-related signal (neutron flux) up to 20% and 40%, respectively.

It is theorized by the present inventors that the increase in neutron signal may be related to the neutron scattering properties of the shielding material of a source holder. Referring to tungsten as an exemplary shielding material of a source holder in a neutron detector, tungsten may act both as a shield against gamma radiation and as a method of scattering fast neutrons that would otherwise miss hitting the target material.

Figure 3:
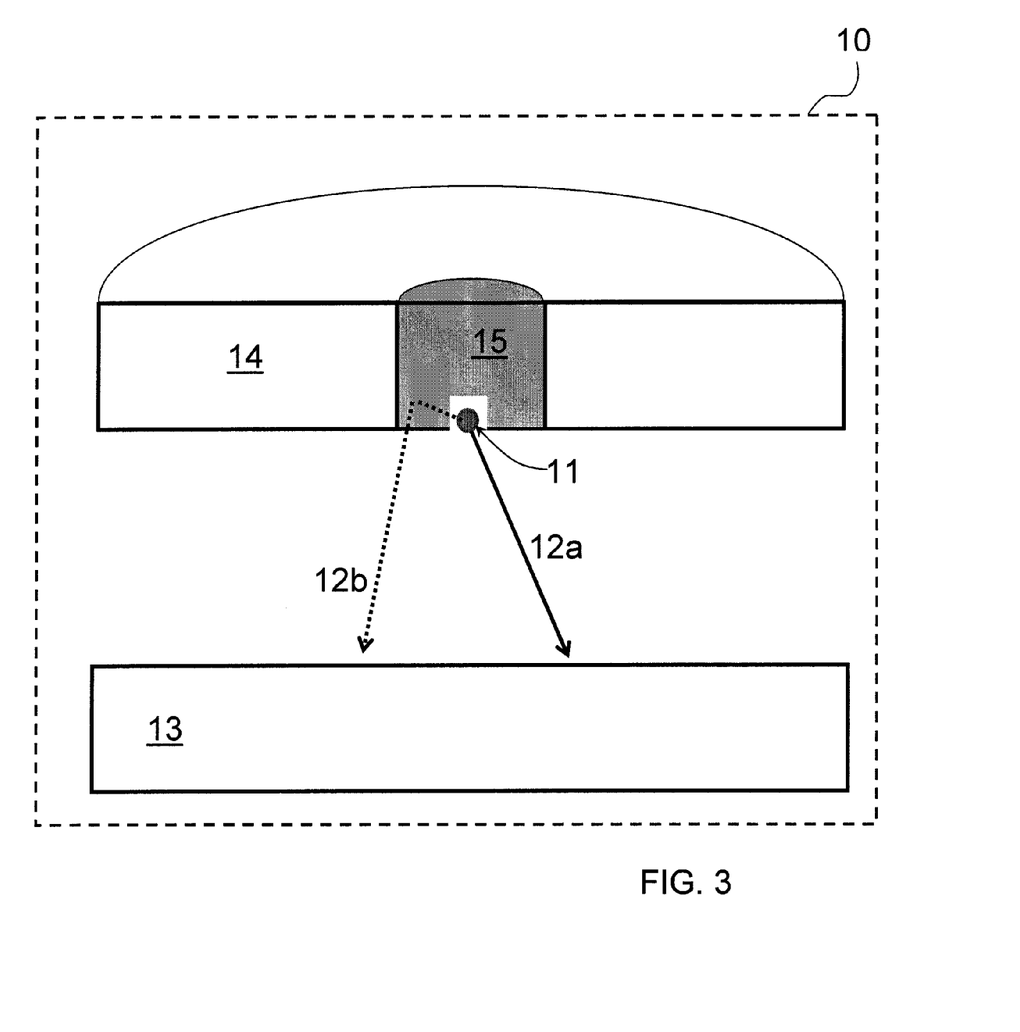
FIG. 3 shows a cross-sectional view of a moisture analyzer according to embodiments of the present disclosure.

In particular, FIG. 3 shows a cross sectional view of a moisture analyzer 10 according to embodiments of the present disclosure having a toroidal (donut) shape detector 14, such that there is a hole at the center of the detector 14. A neutron source 11 is partially surrounded by a shielding source holder 15 and positioned in the center of the detector 14. The shielding source holder 15 is made of a shielding material, such as tungsten. As shown, the source holder 15 surrounds all sides of the neutron source 11 except for a side facing the target 13, such that the shielding source holder 15 is between the neutron source 11 and the detector 14.

The neutron source 11 emits fast neutrons 12a, 12b. In particular, fast neutrons 12a are emitted from neutron source 11 in a direction directly toward the target 13. Fast neutrons 12b are initially emitted from neutron source 11 in a direction away from the target 13 and into the shielding material of the shielding source holder 15. Depending on the neutron scattering properties of the shielding material of the shielding source holder 15, the likelihood of fast neutrons 12b being redirected toward the target 13 may increase. Although shielding source holder 15 does not affect the fast neutrons 12a initially directed toward target 13, shielding source holder 15 enables another mechanism of neutron scattering, which may increase the amount of fast neutrons 12b that hit target 13, and thus increase the total amount of fast neutrons 12a, 12b capable of neutron moderation.

Figure 4:
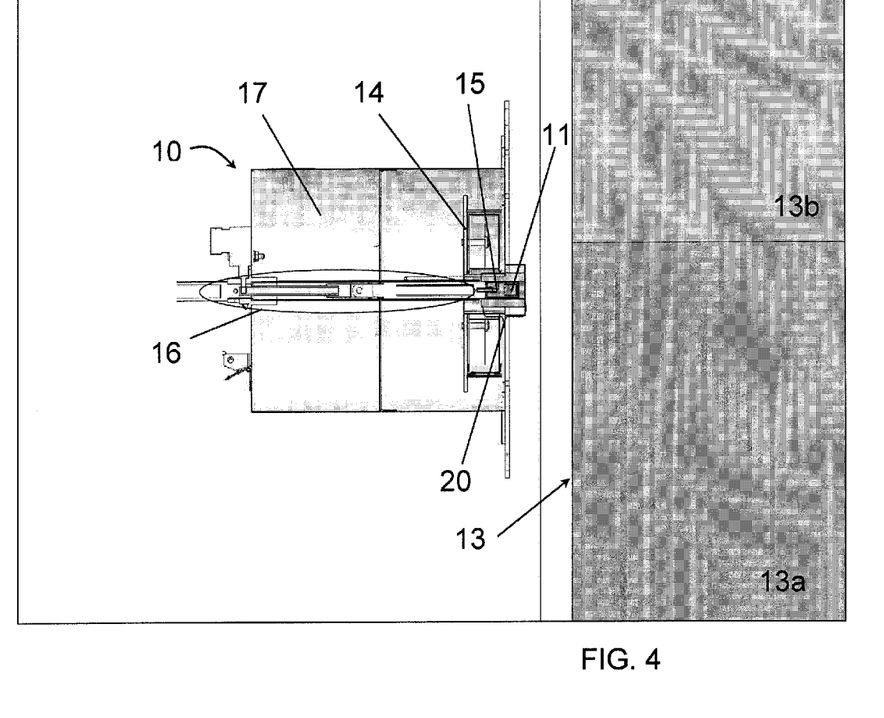
FIG. 4 shows a cross-sectional view of another embodiment of a moisture analyzer in accordance with the present disclosure.

FIG. 4 shows a cross-sectional view of another embodiment of a moisture analyzer in accordance with the present disclosure. The moisture analyzer 10 of FIG. 4 has an ion chamber detector 14 and a neutron source 11 adjacent to the detector 14. The neutron source 11 has a shielding source holder 15 surrounding the neutron source 11, which may together be referred to as a neutron source assembly 20. The neutron source assembly 20 is inserted in the center of the detector 14 (thus positioning the neutron source 11 in the center of the detector 14) and held in place with a source handle assembly 16. The ion chamber detector 14 is covered with an ion chamber cover 17, which also acts to support the source handle assembly 16. Moisture analyzer 10 is directed to a target 13, such that the neutron source 11 is closest to the target 13. As shown, target 13 may include one or more materials, 13a and 13b.

Figure 5A:
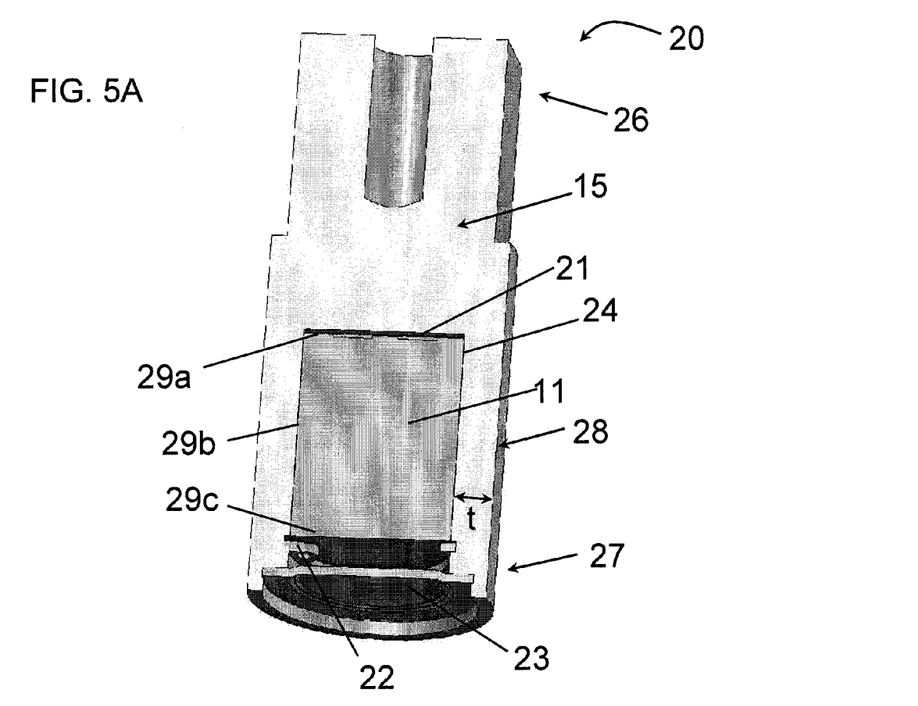
FIGS. 5A and 5B show a cross-sectional view and a perspective view, respectively, of a neutron source assembly according to embodiments of the present disclosure.
Figure 5B:
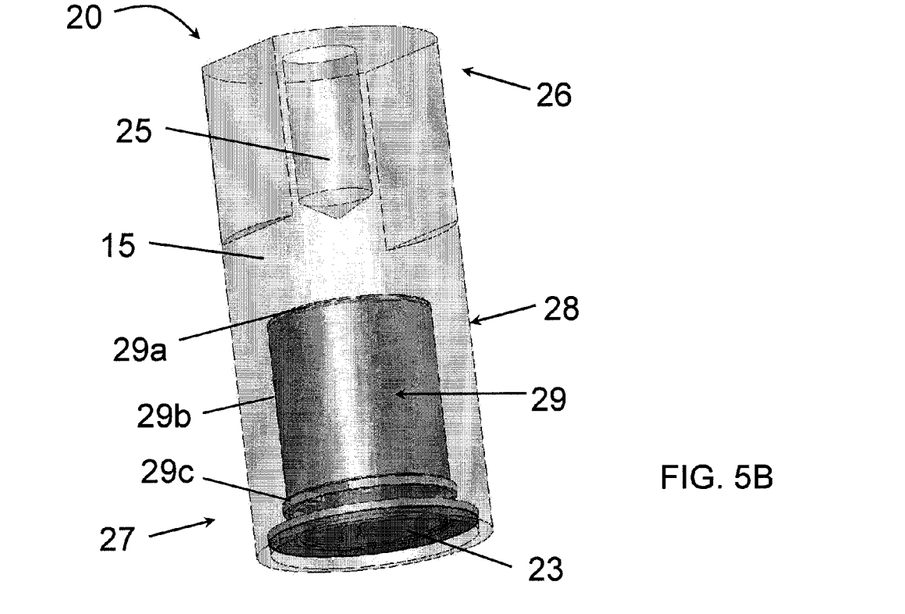

Close perspective and cross-sectional views of components of an exemplary neutron source assembly 20 are shown in FIGS. 5A and 5B. In particular, FIG. 5A shows a cross-sectional view and FIG. 5B shows a perspective view of a neutron source assembly 20 having a neutron source 11 surrounded by a shielding source holder 15. Shielding source holder 15 is made of gamma shielding material such as tungsten. In the embodiment shown, shielding source holder 15 is cylindrical in shape, having a first end 26, a second end 27 opposite from the first end 26, and a substantially circumferential side wall 28. A handle receiver 25 is formed in the first end 26 and a neutron source receiver 24 is formed in the second end 27, opposite from the handle receiver 25. The neutron source receiver 24 is configured to receive the neutron source 11, and the handle receiver 25 is configured to receive a source handle assembly (shown in FIG. 4).

Other sizes and shapes of shielding source holders may be used to shield a neutron source from a detector. For example, a shielding source holder may be shaped as a toroid, a rectangular frame, or any other shape that may at least partially surround the neutron source. Further, a shielding source holder 15 may have a uniform thickness or a non-uniform thickness. For example, as shown in FIGS. 5A and 5B, shielding source holder 15 has a non-uniform thickness t, wherein thickness t is measured from the neutron source receiver 24 to the outer surface of the shielding source holder 15. In particular, the first end 26 of the shielding source holder 15 has a larger thickness than the side wall 28 thickness. Alternatively, other embodiments of a shielding source holder 15 may have a substantially uniform thickness.

Referring again to FIGS. 5A and 5B, neutron source 11 is encapsulated in a stainless steel capsule 29 having a top side 29a, a substantially circumferential side 29b, and a bottom side 29c opposite from the top side 29a. In other embodiments, the capsule may be made of materials other than stainless steel, such as tungsten, lead, etc. A spring washer 21 may be positioned at the top side 29a of the capsule 29, between the capsule 29 and the shielding source holder 15. A circlip 22 may be positioned at the bottom side 29c of the capsule 29 to hold the neutron source 11 in place. Top side 29a and bottom side 29c are labeled relative to their positions in FIGS. 5A and 5B; however, the top and bottom sides may be in various positions within a detector depending on the direction of the detector. A press fit cover 23 may be placed within the neutron source receiver 24 to cover the neutron source 11 and circlip 22.

Those of ordinary skill in the art will appreciate that shielding source holder components may vary, depending on the size and shape of the neutron source and detector. For example, shielding source holders made according to the present disclosure may have various shapes and sizes that position a shielding material between the neutron source and the detector. Additionally, some embodiments of shielding source holders may have additional components, less components, or different configurations of the exemplary components described in FIGS. 5A and 5B, which may be used to position the shielding source holder between the neutron source and the detector.

The inventors of the present disclosure have found through testing that shielding source holders according to embodiments of the present disclosure produce results according to the theory presented above. In particular, the inventors conducted experiments in which a detector reading was produced for detector systems using various target materials, gas-filled ion chambers, and shielding materials and control detector systems using no target or no shielding material. The experiments show that detector systems using shielding source holders according to the present disclosure have low background (from gamma shielding) as well as enhanced neutron signals. Neutron signal, as defined herein, is the resulting signal determined by subtracting the amount of background from the total signal reading. In an exemplary control test using a target material made of polytetrafluoroethylene, a plastic having no hydrogen, zero neutron signal was produced, thus showing neutron signals are produced from hydrogen within target materials. Because the signal produced from a detector system having no target also results in zero neutron signal, target material having no hydrogen results in a neutron signal equal to that of no target. A target made of material having no hydrogen is referred to herein as a "blank target."

Figure 6:
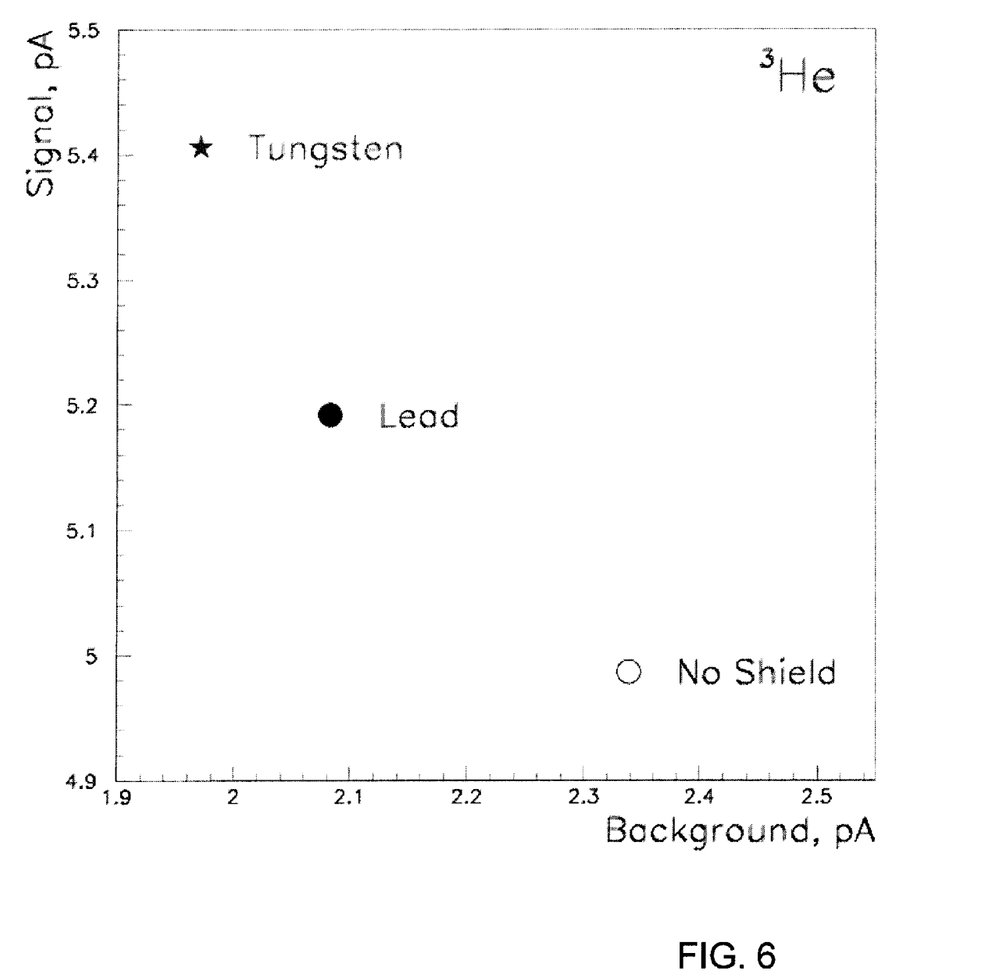
FIG. 6 is a graph of the amount of signal and background detected in moisture analyzers according to embodiments of the present disclosure.

Referring now to FIG. 6, detector readings (produced in the form of current) are shown for a moisture analyzer having a He-3-filled ion chamber and a target made of polyethylene. Detector readings not related to the target are considered background, while detector readings obtained from the presence of the polyethylene target are considered as the total signal. One reading was taken using a shielding source holder made of tungsten; one reading was taken using a shielding source holder made of lead; and another reading was taken using no shielding source holder. As shown, shielding source holders made of lead, and especially tungsten, suppress the background and at the same time increase the total signal.

Figure 7:
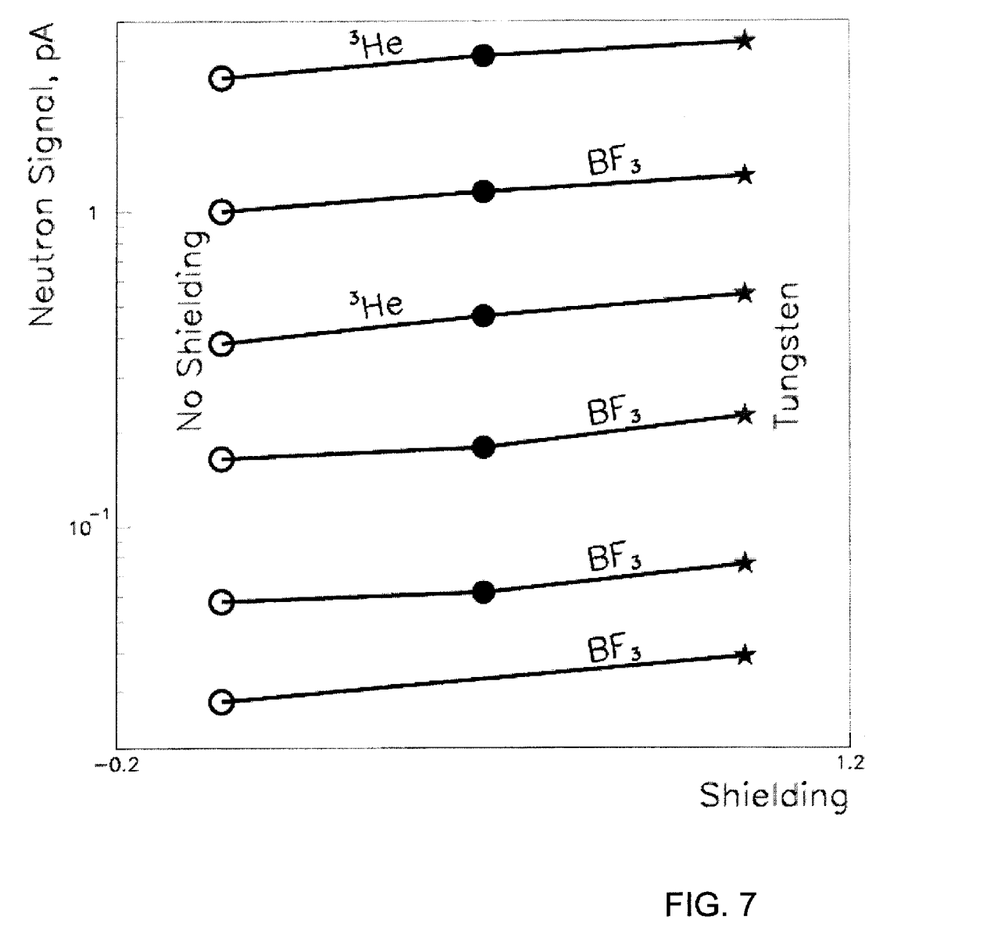
FIG. 7 is a graph of the amount of neutron signal detected in detector systems according to embodiments of the present disclosure.

The amount of background reduction and neutron signal enhancement in embodiments according to the present disclosure was further analyzed and compared with conventional detector systems. Data showing background reduction is shown in Table 1 below and data showing neutron signal enhancement is shown in FIG. 7 and Table 2 below.

In particular, as shown in Table 1, the amount of background from gamma radiation is shown in a detector system having a He-3-filled ion chamber and a detector system having a $BF_3$-filled ion chamber, wherein each detector system was tested with a tungsten shielding source holder, a lead shielding source holder, and no shielding source holder.

TABLE 1

| Gas | No Shield | Lead | Tungsten |
|---|---|---|---|
| He-3 | 2.339 pA | 2.083 pA | 1.971 pA |
| $BF_3$ | 6.227 pA | 3.791 pA | 3.29 pA |

As shown in Table 1, background from gamma radiation was reduced by about 16% when using a shielding source holder made of tungsten in a He-3-filled ion chamber and by about 47% when using a shielding source holder made of tungsten in a $BF_3$-filled ion chamber. Background from gamma radiation was reduced by about 11% when using a shielding source holder made of lead in a He-3-filled ion chamber and by about 39% when using a shielding source holder made of lead in a $BF_3$-filled ion chamber.

Referring now to FIG. 7, neutron signal is enhanced by using shielding source holders according to embodiments of the present disclosure. In particular, detector systems having different gas-filled ion chambers and different target materials each exhibited increased neutron signals when using shielding source holders made of lead and especially tungsten. The values of the neutron signals produced from each detector system of FIG. 7 are shown in Table 2 below.

TABLE 2

| Gas | Target | No Shield | Lead | Lead Ratio | Tungsten | Tungsten Ratio |
|---|---|---|---|---|---|---|
| He-3 | Medium Polyethylene | 2.648 | 3.109 | 3.109/2.648 = 1.17 | 3.435 | 3.435/2.648 = 1.3 |
| He-3 | Small Polyethylene | 0.383 | 0.468 | 1.22 | 0.547 | 1.43 |
| $BF_3$ | Medium Polyethylene | 1.004 | 1.157 | 1.15 | 1.296 | 1.29 |
| $BF_3$ | Small Polyethylene | 0.165 | 0.179 | 1.085 | 0.225 | 1.36 |
| $BF_3$ | Extra-small Polyethylene | 0.058 | 0.062 | 1.069 | 0.076 | 1.31 |
| $BF_3$ | Water | 0.028 | | | 0.039 | 1.39 |

As shown in Table 2, the current readings (measured in pA) are shown for detector systems having He-3- and $BF_3$-filled ion chambers and targets of different sizes and materials with and without shielding source holders. Specifically, three sizes of polyethylene targets were tested, medium, small, and extra small, and a water target was tested. The larger polyethylene targets, which have more hydrogen, produced larger neutron signals. Further, the neutron signals produced in detector systems using lead shielding source holders each produced neutron signals higher than in similar detector systems using no shielding source holders. Likewise, the neutron signals produced in detector systems using tungsten shielding source holders each produced neutron signals higher than in similar detector systems using lead shielding source holders. Thus, the inventors of the present disclosure have found that neutron signal may be enhanced using shielding source holders made of lead and especially tungsten.

The lead ratios and tungsten ratios show the amount of increase in neutron flux when using a shielding source holder compared to detector systems that do not use a shield. These exemplary results show an increase in neutron flux in detector systems using shielding source holders made of shielding material of the present disclosure.

The neutron signals for each case study shown above in Table 2 were calculated by subtracting the signal detected using no target (or a blank target) from the total signal detected using a target made of moderating material. Table 3 shows exemplary calculations for the detector system using a $BF_3$-filled ion chamber and a medium-sized polyethylene target.

TABLE 3

| | No Shield | Tungsten | Ratio |
|---|---|---|---|
| No Target | 6.227 pA | 3.29 pA | |
| Med Poly total signal | 7.231 pA | 4.586 pA | |
| Med Poly neutron signal | 7.231 − 6.227 = 1.004 pA | 4.586 − 3.29 = 1.296 pA | 1.29 |

As shown in Table 3, the neutron signal for a medium-sized polyethylene target was calculated in detector system having no shield and a tungsten shield. In particular, the neutron signals for each case was calculated by subtracting the signal detected using no target (or a blank target) from the total signal detected using a target made of moderating material. The reading for the detector system having no shielding source holder (1.004 pA) was lower than the reading for the detector system having a shielding source holder made of tungsten (1.296 pA). Further, the readings show that the number of neutrons hitting the detector is 1.29 times more with tungsten shielding than without. These exemplary results show increased background readings in detector systems having no shielding source holder and increased neutron signals in detector systems having shielding source holders according to the present disclosure.

Methods of measuring neutron signals using shielding source holders, such as the ones described above, are also within the scope of the present disclosure. In particular, improvements in producing neutron signals while also decreasing gamma background, provided by shielding source holders, may be measured using a three-phase experiment. In the first phase, background is detected for a detector system with a shielding source holder and without a shielding source holder. In particular, background may be detected in a detector system having no target, or alternatively, a blank target (i.e., a target made of material containing no hydrogen), and with a shielding source holder surrounding a portion of the neutron source. The shielding source holder may then be removed and the detector system may be cleaned. Background may then be detected in the cleaned detector system having no shielding source holder surrounding the neutron source. It should be recognized that background may be detected in a detector system with a shielding source holder before or after background is detected in the detector system without a shielding source holder.

In the second phase, a target material made of hydrogen-containing material is placed within the detector system, and total signal is measured for the detector system with and without the shielding source holder. In particular, the total signal is measured for the detector system with the shielding source holder used in phase one. The shielding source holder may then be removed and the total signal is measured for the detector system having no shielding source holder. It should be recognized that total signal may be measured in the detector system with a shielding source holder before or after total signal is measured in the detector system without a shielding source holder.

In the third phase, neutron signal for the detector system with and without a shielding source holder may be determined by subtracting the background from the total signal, which were measured in phases one and two, respectively. In particular, the neutron signal for the detector system with a shielding source holder may be determined by subtracting the background measured by the detector system with the shielding source holder in phase one from the total signal measured by the detector system with the shielding source holder in phase two. The neutron signal for the detector system with no shielding source holder may be determined by subtracting the background measured by the detector system with no shielding source holder in phase one from the total signal measured by the detector system with no shielding source holder in phase two.

A detector system used for the above described methods may include, for example, an ion chamber detector, proportional counters, fission chambers, or scintillator detectors. In particular, a detector system, or analyzer, may include detector systems used to measure the hydrogen content (e.g., moisture) in a sample (target). A shielding source holder of the present disclosure made of shielding material, such as lead or tungsten, may suppress unwanted background signal and at the same time increase the neutron flux, thus increasing the useful signal.

Advantageously, increased neutron signals, and thus a higher neutron flux, may allow for a reduced amount of time for detection and moisture analysis. Inventors of the present disclosure have found that by using shielding source holders made of tungsten, enhanced neutron signals may be obtained while also decreasing the amount of background detected. In particular, shielding source holders partially surround a neutron source so as to shield gamma radiation released from the neutron source from the detector.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed is:

1. An analyzer comprising:
   a detector; and
   a neutron source assembly adjacent to the detector, the neutron source assembly comprising:
     a neutron source; and
     a shielding source holder positioned between the neutron source and the detector;
     wherein the shielding source holder comprises a gamma shielding material.

2. The analyzer of claim 1, further comprising a target comprising a material selected from water, graphite, alcohol, oil, coke, iron pellets, hydrocarbon, polyethylene, polypropylene, and polystyrene.

3. The analyzer of claim 1, wherein the shielding source holder comprises lead.

4. The analyzer of claim 1, wherein the shielding source holder comprises tungsten.

5. The analyzer of claim 1, wherein the detector comprises an ion chamber filled with a gas selected from He-3 and $BF_3$.

6. The analyzer of claim 1, wherein the shielding source holder comprises a first end, a second end opposite the first end, and a substantially circumferential side wall.

7. The analyzer of claim 6, wherein the shielding source holder comprises a handle receiver formed in the first end and a neutron source receiver formed in the second end, opposite from the handle receiver, wherein the neutron source receiver is configured to receive the neutron source, and wherein the handle receiver is configured to receive a source handle assembly.

8. The analyzer of claim 7, further comprising a press fit cover disposed within the neutron source receiver.

9. The analyzer of claim 1, wherein the neutron source is encapsulated in a stainless steel capsule.

10. The analyzer of claim 9, wherein the neutron source assembly further comprises a spring washer disposed between a top side of the capsule and the shielding source holder.

11. The analyzer of claim 9, wherein a circlip is disposed at a bottom side of the capsule.

12. The analyzer of claim 1, wherein the shielding source holder partially surrounds the neutron source, such that the shielding source holder is between the neutron source and the detector.

13. A method for measuring neutron signals, the method comprising:
   detecting background in a detector system;

placing a target within the detector system after detecting background;

measuring a total signal for the detector system having the target therein; and determining a neutron signal for the detector system, wherein the neutron signal is the resulting signal determined by subtracting the amount of background detected by the detector system from the total signal.

14. The method of claim 13, wherein the detector system comprises:

a detector; and a neutron source assembly adjacent to the detector, the neutron source assembly comprising:

a neutron source; and a shielding source holder.

15. The method of claim 14, wherein the shielding source holder comprises a material selected from lead and tungsten.

16. The method of claim 15, wherein the detector comprises an ion chamber filled with a gas selected from He-3 and $BF_3$.

17. The method of claim 14, further comprising measuring neutron signals for the detector system without the shielding source holder, comprising:

detecting background in the detector system, wherein the shielding source holder is removed;

placing a target within the detector system;

measuring total signal for the detector system having the target therein; and determining the neutron signal for the detector system, wherein determining comprises subtracting the background detected by the detector system from the total signal measured by the detector system.

18. The method of claim 13, wherein the target is selected from water, graphite, alcohol, oil, coke, iron pellets, hydrocarbon, polyethylene, polypropylene, and polystyrene.

19. The method of claim 13, wherein detecting background in the detector system comprises disposing a blank target in the detector system.

20. The method of claim 19, further comprising removing the blank target.

* * * * *